(12) United States Patent
Oka et al.

(10) Patent No.: US 6,808,496 B2
(45) Date of Patent: Oct. 26, 2004

(54) OSCILLOMETRIC AUTOMATIC BLOOD-PRESSURE MEASURING APPARATUS

(75) Inventors: Tohru Oka, Komaki (JP); Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 179 days.

(21) Appl. No.: 10/286,900

(22) Filed: Nov. 4, 2002

(65) Prior Publication Data

US 2003/0097074 A1 May 22, 2003

(30) Foreign Application Priority Data

Nov. 19, 2001 (JP) ........................................ 2001-352547

(51) Int. Cl.⁷ ................................................. A61B 5/00
(52) U.S. Cl. ...................... 600/485; 600/490; 600/494; 600/500
(58) Field of Search .............................. 600/485, 490, 600/493–6, 500

(56) References Cited

U.S. PATENT DOCUMENTS

| | | | | |
|---|---|---|---|---|
| 5,865,756 A | * | 2/1999 | Peel, III | 600/490 |
| 6,120,456 A | * | 9/2000 | Oka et al. | 600/485 |
| 6,423,010 B1 | * | 7/2002 | Friedman et al. | 600/494 |
| 6,582,374 B2 | * | 6/2003 | Yokozeki | 600/494 |
| 6,602,198 B2 | * | 8/2003 | Yokozeki | 600/485 |

FOREIGN PATENT DOCUMENTS

EP 1 080 685 3/2001

* cited by examiner

Primary Examiner—Robert L. Nasser
(74) Attorney, Agent, or Firm—Oliff & Berridge, PLC (57) ABSTRACT

An oscillometric automatic blood-pressure measuring apparatus, including an inflatable cuff which is adapted to be wound around a portion of a living subject, so as to detect respective amplitudes of a plurality of heartbeat-synchronous pulses of a cuff pulse wave as an oscillatory component that is produced in the cuff in synchronism with heartbeats of the subject in a cuff-pressure change process in which a cuff pressure as a pressure in the cuff is changed, a cuff-pulse-wave-amplitude correcting device for correcting the respective amplitudes of the respective pulses of the cuff pulse wave, according to a predetermined non-linear relationship between difference between cuff pressure and subject's mean blood pressure, and amplitude of cuff pulse wave, and a blood-pressure determining device for determining a blood pressure of the subject based on a change of the corrected amplitudes of the cuff pulse wave.

10 Claims, 6 Drawing Sheets

OSCILLOMETRIC AUTOMATIC BLOOD-PRESSURE MEASURING APPARATUS

BACKGROUND OF THE INVENTION

1. Field of the Invention

The present invention relates to an automatic blood-pressure measuring apparatus for automatically measuring a blood pressure of a living subject according to so-called oscillometric method.

2. Related Art Statement

Figure 1A:
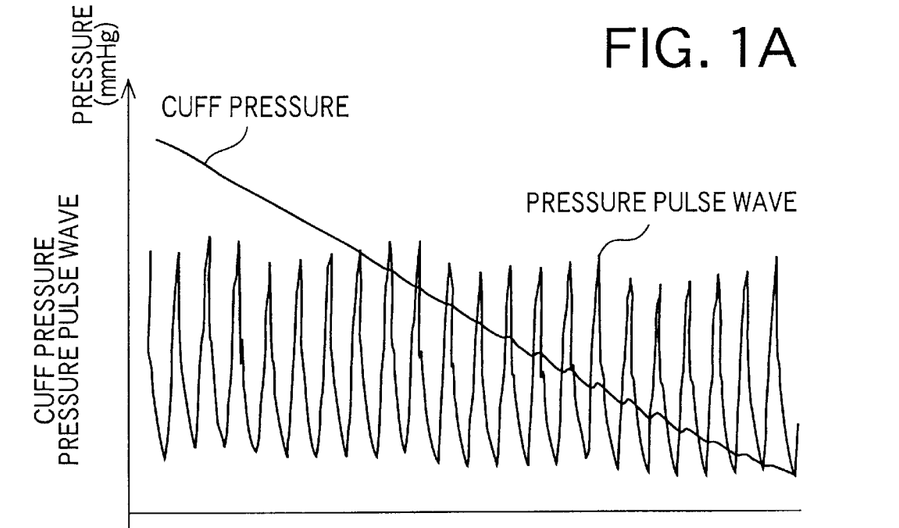
FIG. 1A is a graph showing, as a heartbeat-synchronous wave, a pressure pulse wave that is produced in an artery in a process in which cuff pressure is slowly decreased.
Figure 1B:
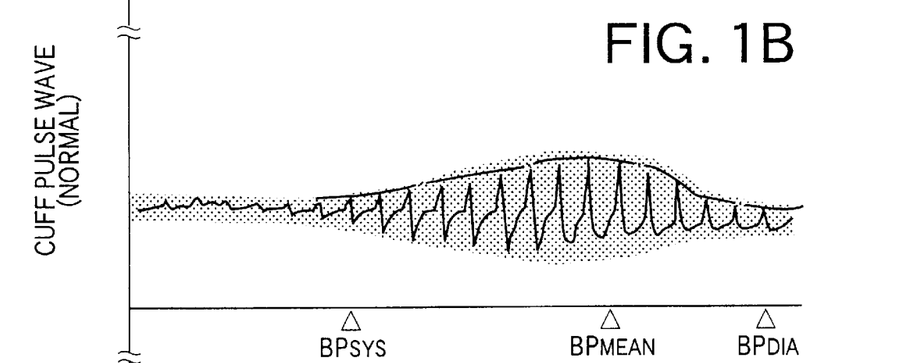
FIG. 1B is a graph showing, as another heartbeat-synchronous wave, a normal cuff pulse wave that is detected from a cuff in the same process.

In an oscillometric blood-pressure measurement, a pressing pressure of a cuff wound around, e.g., an upper arm of a living subject, that is, a cuff pressure is slowly changed, and a blood pressure of the subject is measured based on change of amplitudes of a plurality of heartbeat-synchronous pulses of a cuff pulse wave as an oscillatory component produced in the cuff during that process, with respect to change of the cuff pressure. FIG. 1B shows the heartbeat-synchronous pulses of the cuff pulse wave extracted from the cuff pressure, and a systolic and a diastolic blood pressure values are determined based on greatest-slope points or inflection points of an envelope, indicated at one-dot chain line in FIG. 1B, that passes through the greatest one of respective amplitudes of the successive pulses of the cuff pulse wave. An automatic blood-pressure measuring apparatus that employs the oscillometric method can measure blood pressure at a region, such as anterior region of neck, finger, or inferior limb, where it is considerably difficult to measure blood pressure according to so-called microphone method. In addition, though the microphone method essentially requires that a microphone be accurately placed right above an artery, the oscillometric method just requires that a cuff be wound, and thus can be easily carried out without needing a special skill of a measuring person. Moreover, the oscillometric method can be used at noisy places, and can also be used to measure blood pressure from children who produce small Korotokoff sounds only, or patients falling in shock. Thus, the automatic blood-pressure measuring apparatus employing the oscillometric method is widely used.

Figure 1C:
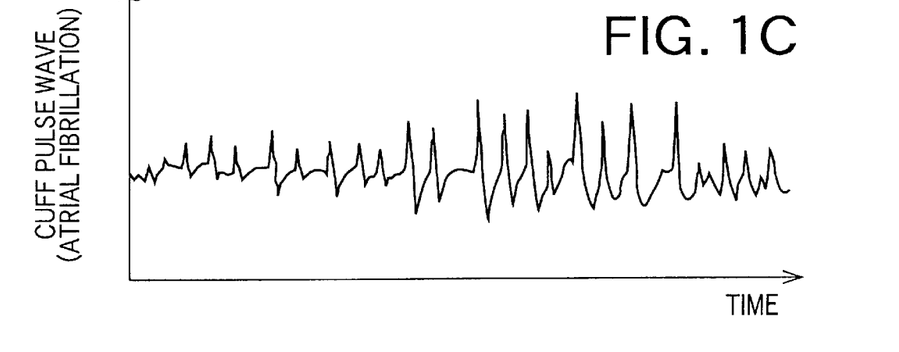
FIG. 1C is a graph showing a cuff pulse wave that is detected from a cuff in the same process, when arrhythmia such as atrial fibrillation occurs.

As explained above, in the oscillometric method, a blood pressure is measured based on change of respective amplitudes of respective pulses of a cuff pulse wave, produced in a cuff during a slow changing of a cuff pressure, with respect to the change of the cuff pressure. However, in a particular case where arrhythmia such as atrial fibrillation occurs, as shown in FIG. 1C, a waveform of a cuff pulse wave is deformed, and accordingly an envelope connecting respective upper ends of respective amplitudes of the cuff pulse wave along the axis of cuff pressure is also deformed. Thus, a blood pressure cannot be measured, or an inaccurate blood pressure is measured.

SUMMARY OF THE INVENTION

It is therefore an object of the present invention to provide an automatic blood-pressure measuring apparatus which can measure blood pressure with high accuracy even in the case where arrhythmia occurs.

Figure 2A:
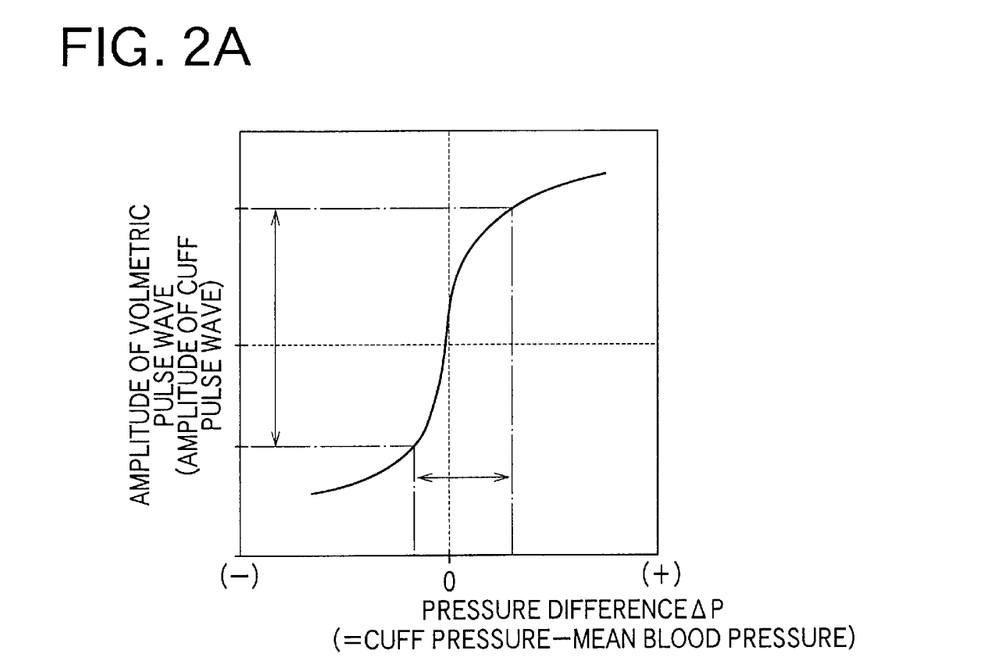
FIG. 2A is a graph showing a non-linear relationship between difference of inner and outer pressures of subject's artery and amplitude of volumetric pulse wave, and additionally explaining the influence of magnitude of pulse pressure.
Figure 2B:
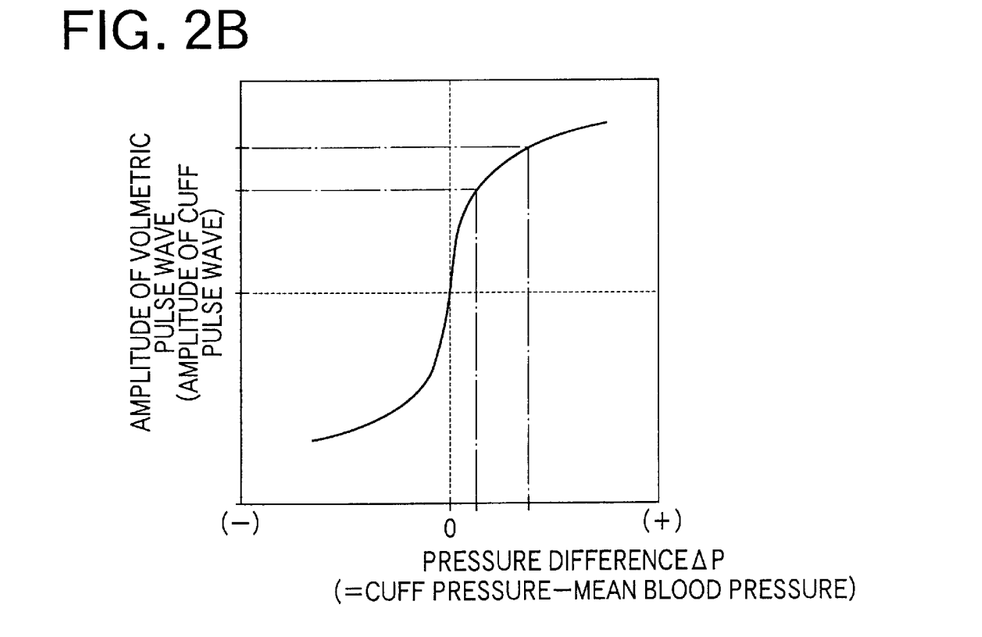
FIG. 2B is a graph showing the non-linear relationship and additionally explaining the influence of deviation (or shifting) of pulse pressure.

The inventors have made extensive studies to achieve the above-indicated object, and have found the following facts: In the oscillometric blood-pressure measuring method, a cuff pressure, i.e., a pressure in a cuff to press, e.g., an upper arm of a living subject is slowly changed (e.g., lowered), as shown in FIG. 1A, then a pulsatile component mixed with the cuff pressure is extracted as a cuff pulse wave, and a systolic and a mean blood pressure value are determined based on the cuff pressure and an envelope of the cuff pulse wave, i.e., oscillometric waveform, as shown in FIG. 1B. The change of amplitudes in the oscillometric waveform can be explained using an S-shaped non-linear relationship between inner volume and inner pressure of blood vessel, shown in FIGS. 2A and 2B. More specifically described, as shown in FIG. 2A, when pressure difference between inner and outer pressures of blood vessel is around zero, inner volume of the blood vessel largely changes; and, as shown in FIG. 2B, as the inner pressure increases or decreases, the amount of deformation of the blood vessel's wall decreases and accordingly the change of inner volume decreases. Therefore, when the cuff pressure is around a mean blood pressure of the subject, the cuff (i.e., volumetric) pulse wave shows the greatest amplitude corresponding to the greatest pulse pressure (=systolic blood pressure−diastolic blood pressure). As the cuff pressure is changed in a direction away from the mean blood pressure, respective amplitudes of respective pulses of the cuff pulse wave become smaller. Thus, the relationship shown in FIGS. 2A and 2B can explain that when arrhythmia occurs and accordingly an intravascular pressure pulse wave changes and/or a pulse pressure shifts, a cuff pulse wave, i.e., an oscillometric pulse wave that periodically changes with inner volume of blood vessel is deformed and therefore an envelope defined by the cuff pulse wave is also deformed. This envelope cannot be used as a basis for obtaining an accurate blood pressure. Hence, respective amplitudes of successive pulses of a finger-tip pulse wave as a volumetric pulse wave that is detected by a photoelectric-pulse-wave sensor, are used in place of the respective pulse pressures of the successive pulses of the intravascular pressure pulse wave; respective correction factors are determined, according to the relationship shown in FIGS. 2A and 2B, based on respective changes of the respective amplitudes of the successive pulses of the finger-tip pulse wave from the amplitude of the specific pulse at the time of detection of the cuff pressure (i.e., the mean blood pressure) corresponding to the greatest amplitude of the cuff pulse wave; those correction factors are used to correct the respective amplitudes of the corresponding pulses of the cuff pulse wave; and a blood pressure is determined based on an envelope defined by the thus corrected amplitudes of the cuff pulse wave. This blood pressure measurement can be carried out even when arrhythmia occurs, and the accuracy of measured blood pressure value is greatly improved. The present invention has been developed based on these facts.

The above object has been achieved by a first aspect of the present invention according to which there is provided an oscillometric automatic blood-pressure measuring apparatus, comprising an inflatable cuff which is adapted to be wound around a first portion of a living subject, so as to detect respective amplitudes of a plurality of heartbeat-synchronous pulses of a cuff pulse wave as an oscillatory component that is produced in the cuff in synchronism with heartbeats of the subject in a cuff-pressure change process in which a cuff pressure as a pressure in the cuff is changed; a cuff-pulse-wave-amplitude correcting means for correcting the respective amplitudes of the respective pulses of the cuff pulse wave, according to a predetermined non-linear relationship between difference between cuff pressure and subject's mean blood pressure, and amplitude of cuff pulse wave; and a blood-pressure determining means for determining a blood pressure of the subject based on a change of the corrected amplitudes of the cuff pulse wave.

According to this aspect, the cuff-pulse-wave-amplitude correcting means corrects the amplitudes of the cuff pulse wave, according to the non-linear relationship between difference between cuff pressure and subject's mean blood pressure, and amplitude of cuff pulse wave, and the blood-pressure determining means determines the blood pressure of the subject based on the change of the corrected amplitudes of the cuff pulse wave. Thus, even in the case where arrhythmia occurs, a reliable envelope is obtained and accordingly a blood pressure can be measured or an accurate blood pressure can be obtained.

According to a second aspect of the present invention, there is provided an oscillometric automatic blood-pressure measuring apparatus, comprising an inflatable cuff which is adapted to be wound around a first portion of a living subject, so as to detect respective amplitudes of a plurality of heartbeat-synchronous pulses of a cuff pulse wave as an oscillatory component that is produced in the cuff in synchronism with heartbeats of the subject in a cuff-pressure change process in which a cuff pressure as a pressure in the cuff is changed; a pulse-wave detecting device which is worn on a second portion of the subject and which detects, from the second portion, a plurality of heartbeat-synchronous pulses of a pulse wave; a pulse-pressure-correction-factor determining means for determining, based on respective amplitudes of the respective pulses of the pulse wave detected by the pulse-wave detecting device, respective pulse-pressure correction factors to correct respective pulse pressures corresponding to the respective amplitudes of the respective pulses of the pulse wave, to a single value; a mean-blood-pressure storing device which stores a mean blood pressure of the subject; a relationship determining means for determining, based on the mean blood pressure stored by the mean-blood- pressure storing device, a non-linear relationship between difference between cuff pressure and subject's mean blood pressure, and amplitude of cuff pulse wave; a mean-blood-pressure estimating means for estimating, based on the respective pulses of the pulse wave detected by the pulse-wave detecting device, respective estimated mean blood pressure values corresponding to the respective pulses of the cuff pulse wave; a mean-blood-pressure-correction-factor determining means for determining, according to the non-linear relationship determined by the relationship determining means, respective mean-blood-pressure correction factors to correct respective amplitude changes corresponding to respective deviations of the respective estimated mean blood pressure values corresponding to the respective pulses of the cuff pulse wave, from the mean blood pressure stored by the mean-blood-pressure storing device; a cuff-pulse-wave-amplitude correcting means for correcting the respective amplitudes of the cuff pulse wave, based on the respective pulse-pressure correction factors determined by the pulse-pressure-correction-factor determining means and the respective mean-blood-pressure correction factors determined by the mean-blood-pressure-correction-factor determining means; and a blood-pressure determining means for determining a blood pressure of the subject based on a change of the corrected amplitudes of the cuff pulse wave.

According to the second aspect, the pulse-pressure-correction-factor determining means determines, based on amplitudes of the pulse wave, respective pulse-pressure correction factors to correct pulse pressures corresponding to the amplitudes of the pulse wave, to a single value, the relationship determining means determines, based on the mean blood pressure, a non-linear relationship between difference between cuff pressure and subject's mean blood pressure, and amplitude of cuff pulse wave, the mean-blood-pressure estimating means estimates, based on the pulse wave, respective estimated mean blood-pressure values corresponding to respective pulses of the cuff pulse wave, the mean-blood-pressure-correction-factor determining means determines, according to the relationship, respective mean-blood-pressure correction factors to correct respective amplitude changes caused by respective deviations of the respective estimated mean blood pressure values corresponding to the respective pulses of the cuff pulse wave, from the mean blood pressure, the cuff-pulse-wave-amplitude correcting means corrects the amplitudes of the cuff pulse wave, based on the respective pulse-pressure correction factors and the respective mean-blood-pressure correction factors, and the blood-pressure determining means determines the blood pressure of the subject based on the change of the corrected amplitudes of the cuff pulse wave. The envelope defined by the corrected cuff pulse wave is accurate, and the blood pressure can be easily determined based on the accurate envelope. Thus, even in the case where arrhythmia occurs, a blood pressure can be measured or an accurate blood pressure can be obtained.

Preferably, the present apparatus further includes a temporary-mean-blood-pressure determining means for determining, as a temporary mean blood pressure of the subject, a cuff pressure corresponding to the greatest one of the amplitudes of the cuff pulse wave by using an envelope defined by the amplitudes before correction, and the mean-blood-pressure storing device stores, as the mean blood pressure of the subject, the temporary mean blood pressure determined by the temporary-mean-blood-pressure determining means. According to this feature, an accurate mean blood pressure of the subject is obtained and accordingly a blood pressure can be measured with high accuracy even in the case where arrhythmia occurs.

BRIEF DESCRIPTION OF THE DRAWINGS

The above and optional objects, features, and advantages of the present invention will be better understood by reading the following detailed description of the preferred embodiments of the invention when considered in conjunction with the drawings, in which.

DETAILED DESCRIPTION OF PREFERRED EMBODIMENTS

Figure 3:
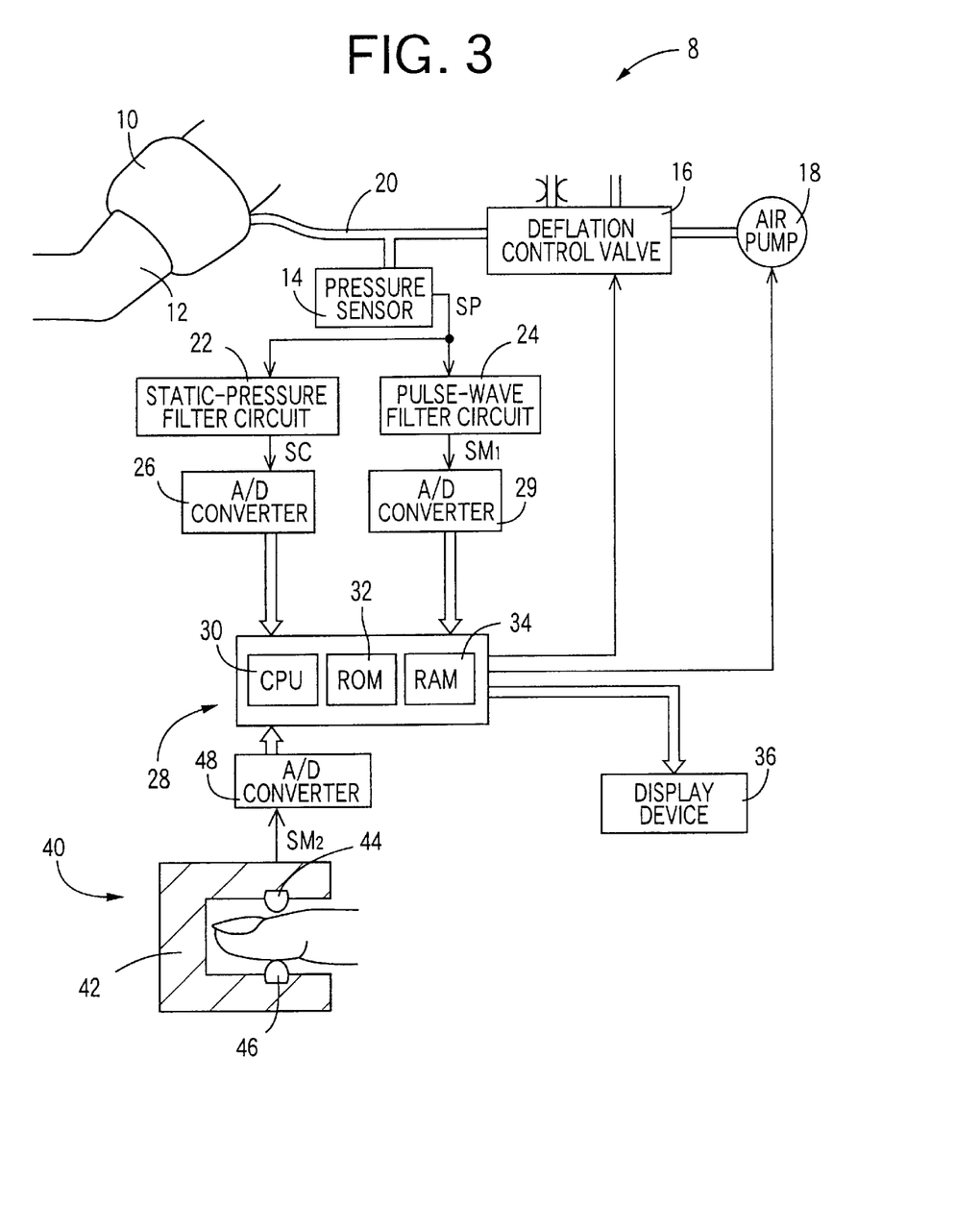
FIG. 3 is a diagrammatic view for explaining an essential portion of a construction of an automatic blood-pressure measuring apparatus as one embodiment of the present invention.

Hereinafter, there will be described an embodiment of the present invention in detail by reference to the drawings. FIG. 3 shows a diagrammatic view for explaining a construction of an automatic blood-pressure measuring apparatus 8 to which the present invention is applied.

In the figure, the oscillometric automatic blood-pressure measuring apparatus 8 includes an inflatable cuff 10 which includes a belt-like cloth bag and a rubber bag accommodated in the cloth bag and which is wound around, e.g., a right upper arm 12 of a patient. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure $P_K$ in the cuff 10, and supplies a pressure signal SP representing the detected pressure $P_K$, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff-pressure signal SC representing the static pressure in the cuff 10. The cuff-pressure signal SC is supplied to a control device 28 via an A/D converter 26. The pulse-wave filter circuit 24 includes a band-pass filter and extracts, from the pressure signal SP, an oscillatory component, i.e., a cuff-pulse-wave signal $SM_1$. The cuff-pulse-wave signal $SM_1$ is supplied to the control device 28 via an A/D converter 29. The cuff-pulse-wave signal $SM_1$ represents a cuff pulse wave $W_K$ as a first volumetric pulse wave including successive heartbeat-synchronous pulses having respective amplitudes.

The control device 28 is provided by a so-called microcomputer including a CPU 30, a ROM 32, a RAM 34 and an I/O port, not shown. The CPU 30 processes signals according to the control programs pre-stored in the ROM 32 by utilizing the temporary-storage function of the RAM 34, and supplies drive signals via the I/O port to respective drive circuits, not shown, associated with the deflation control valve 16 and the air pump 18 so as to change the air pressure in the cuff 10. In addition, the CPU 30 determines, based on change of the respective amplitudes of the successive pulses of the cuff pulse wave $W_K$ represented by the cuff-pulse-wave signal $SM_1$, a blood pressure value BP of the patient, such as a systolic blood pressure value $BP_{SYS}$ and/or a diastolic blood pressure value $BP_{DIA}$, according to the oscillometric method, and additionally operates a display device 36 to display the thus measured blood-pressure values BP.

A photoelectric-pulse-wave sensor 40 functioning as a volumetric-pulse-wave detecting device detects a volumetric pulse wave (i.e., a plethysmograph) representing a volume of a peripheral blood vessel of the subject. The sensor 40 is worn on, e.g., a tip portion of a finger of the other arm than the arm around which the cuff 10 is wound. The photoelectric-pulse-wave sensor 40 has the same construction as that of a known sensor used to detect pulsation. More specifically described, the sensor 40 includes a housing 42 that can accommodate a portion of the subject, such as a tip portion of a finger; a light emitting element 44 as a light source that is disposed on one of opposite walls of the housing 42 and emits, toward the skin of the subject, a red or infrared light in a frequency range that is reflected by hemoglobin, preferably a light having a wavelength of, e.g., about 800 nm, that is not influenced by blood oxygen saturation; and a light receiving element 46 that is disposed on the other wall of the housing 42 such that the light receiving element 46 is opposed to the light emitting element 44, and detects the light transmitted through the portion of the subject. The light receiving element 46 produces a photoelectric-pulse-wave signal $SM_2$ representing the detected amount of light, i.e., volume of the blood present in the capillaries, and supplies the signal $SM_2$ to the control device 28 via an A/D converter 48. The photoelectric-pulse-wave signal $SM_2$ represents a photoelectric pulse wave as a second volumetric pulse wave including successive heartbeat-synchronous pulses having respective amplitudes.

Figure 4:
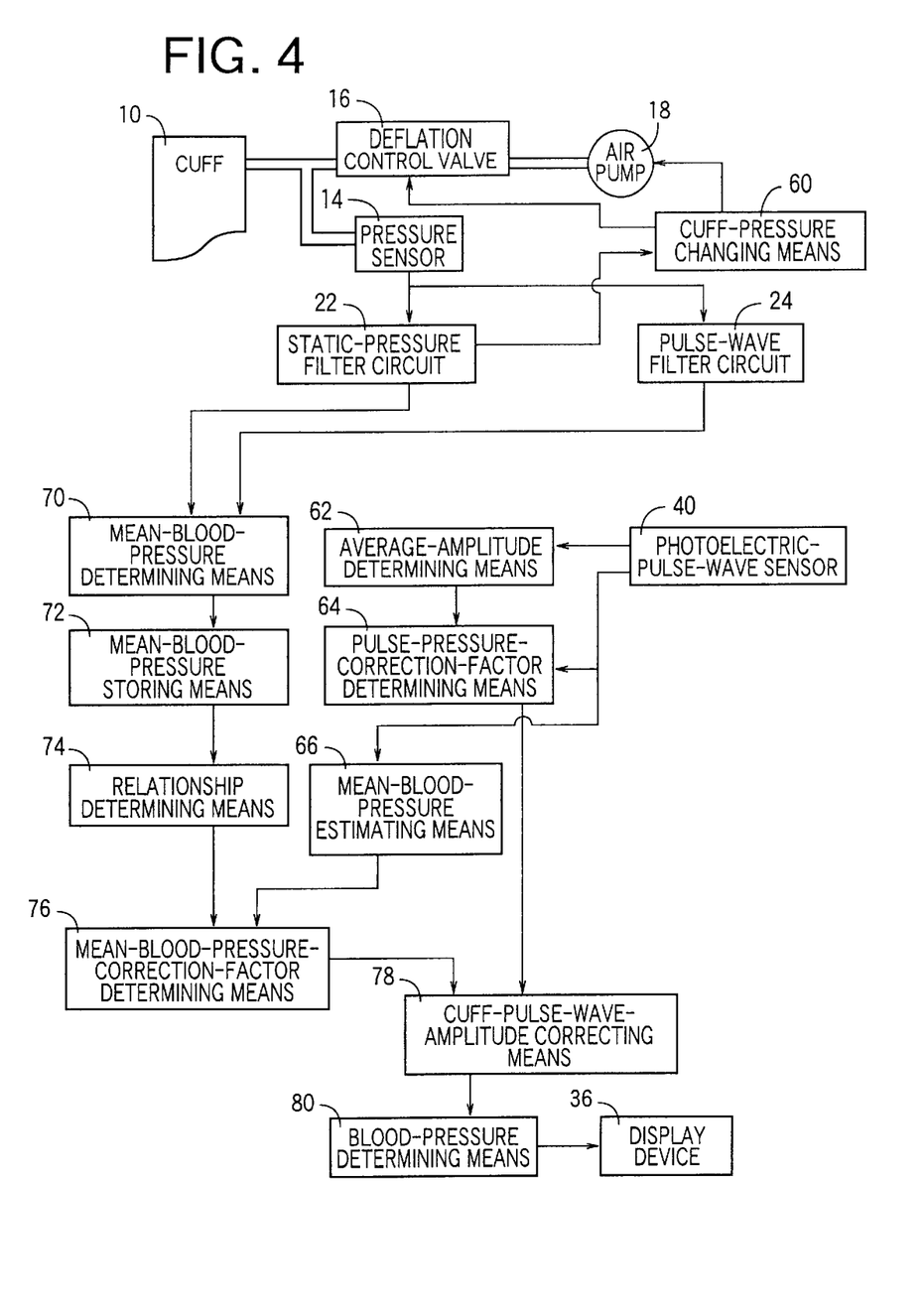
FIG. 4 is a diagrammatic view for explaining essential control functions of a control device employed in the apparatus of FIG. 3.

FIG. 4 is a diagrammatic view for explaining essential control functions of the control device 28. In the figure, a cuff-pressure changing means 60 operates, based on the cuff-pressure signal SC supplied from the static-pressure filter circuit 22, the air pump 18 and the deflation control valve 16 to quickly increase the pressing pressure of the cuff 10, i.e., the cuff pressure $P_C$ up to a prescribed first target pressure $P_{CM1}$ (e.g., 180 mmHg) which would be higher than a systolic blood-pressure value $BP_{SYS}$ of the patient and subsequently slowly decrease the cuff pressure $P_C$, at a rate of from 2 to 3 mmHg/sec, down to a prescribed second target pressure $P_{CM2}$ (e.g., 60 mmHg) which would be lower than a diastolic blood-pressure value $BP_{DIA}$ of the patient.

An average-amplitude determining means 62 determines respective amplitudes $AL_n$ of respective pulses $WL_n$ of the photoelectric pulse wave continuously detected by the photoelectric-pulse-wave sensor 40 while the cuff pressure $P_C$ is slowly decreased by the cuff-pressure changing means 60, and additionally determines an average of the thus determined amplitudes $AL_n$, i.e., an average amplitude $AL_{per}$. A pulse-pressure-correction-factor determining means 64 determines a ratio of the average amplitude $AL_{per}$ determined by the average-amplitude determining means 62, to each of the respective amplitudes $AL_n$ of the respective pulses $WL_n$ of the photoelectric pulse wave, and thereby provides respective pulse-pressure or first correction factors $K_{1n}$ for the respective pulses $WL_n$ corresponding to respective pulse pressures (=systolic blood pressure–diastolic blood pressure) of successive heartbeat-synchronous pulses of a pressure pulse wave produced in an artery during the pressing of the cuff 10. That is, the determining means 64 determines the respective first correction factors $K_{1n}$ for the respective pulses $WL_n$ of the photoelectric pulse wave, according to Expression 1. If the first correction factors $K_n$ are multiplied by the respective amplitudes $AL_n$ of the pulses $WL_n$, then the average amplitude $Al_{per}$ is obtained for all the pulses $WL_n$. Thus, the first correction factors $K_n$ are factors for modifying the respective amplitudes $AL_n$ of the pulses $WL_n$, or the respective pulse pressures of the respective pulses of the pressure pulse wave, to a single value (the average amplitude $Al_{per}$ or an average pulse pressure), and thereby removing the variation of the amplitudes $AL_n$ of the pulses $WL_n$, or the variation of the pulse pressures, during the slow decreasing of the cuff pressure $P_C$. The number, n, indicates an integer.

$$K_{1n}=AL_{per}/AL_n \quad \text{(Expression 1)}$$

A mean-blood-pressure estimating means 66 determines, based on respective magnitudes of the respective pulses $WL_n$ of the photoelectric pulse wave that correspond to the respective pulses of the pressure pulse wave, respective estimated mean blood pressure values corresponding to the respective pulses of the pressure pulse wave, according to a pre-determined relationship, pre-stored in the ROM 32. For example, a center of gravity of an area defined by a waveform of each pulse $WL_n$ is determined, and an estimated blood pressure value is determined based on a magnitude of the center of gravity according to a pre-determined relationship, e.g., a relationship between blood pressure and magnitude of photoelectric pulse wave that is determined beforehand based on systolic and diastolic blood pressure values measured using the cuff 10 and an amplitude of one pulse of the photoelectric pulse wave. Generally, the magnitude of a center of gravity of one pulse of a photoelectric pulse wave may be replaced with one third of a pulse pressure PM represented by the amplitude of the one pulse.

A mean-blood-pressure determining means 70 determines a mean blood pressure, $BP_{MEAN}$, of the patient, e.g., a temporary mean blood pressure, $BP_{AVE}$, of the patient (or the subject) as a cuff pressure corresponding to the greatest amplitude of the envelope defined by the amplitudes of the cuff pulse wave before correction. A mean-blood-pressure storing means 72 stores, in a memory area of the RAM 34, the thus determined temporary mean blood pressure $BP_{AVE}$. The greatest value of the envelope can be identified with a considerably high accuracy, even if the cuff pulse wave may be deformed due to arrhythmia, and accordingly the temporary mean blood pressure can be determined with a considerably high accuracy. The mean-blood-pressure storing means 72 stores, in addition to the temporary mean blood pressure determined by the mean-blood-pressure determining means 70, the actual amplitude of the cuff pulse wave (i.e., the greatest value of the envelope) at the time of detection of the temporary mean blood pressure. However, the mean-blood-pressure storing means 72 may be arranged to store and keep a mean blood pressure measured in, e.g., the last blood-pressure measurement.

A relationship determining means 74 determines an S-shaped non-linear relationship between pressure difference $\Delta P$ as difference between cuff pressure and subject's mean blood pressure, and amplitude of cuff pulse wave as volumetric pulse wave, based on the mean blood pressure determined by the mean-blood-pressure determining means 70 and the actual amplitude corresponding to the mean blood pressure. More specifically described, a relationship between pressure difference $\Delta P$ (=cuff pressure−mean blood pressure) and amplitude of cuff pulse wave, obtained as a nature of the artery, is pre-stored in the ROM 32, and respective scales of a pressure-difference axis and a cuff-pulse-wave-amplitude axis for the relationship are calibrated based on the actual mean blood pressure $BP_{AVE}$ and the greatest value of the envelope. Thus, for example, a non-linear relationship, as shown in FIG. 2, is obtained.

A mean-blood-pressure-correction-factor determining means 76 determines, according to the non-linear relationship determined by the relationship determining means 74, respective mean-blood-pressure or second correction factors $K_{2n}$ for the respective pulses of the cuff pulse wave, based on respective deviations (i.e., respective differences) of the respective estimated mean blood pressure values corresponding to the respective pulses of the pressure pulse wave or the cuff pulse wave, estimated by the mean-blood-pressure estimating means 66, from the mean blood pressure $PB_{AVE}$ of the patient as the subject, stored by the mean-blood-pressure storing means 72. The respective second correction factors $K_{2n}$ are for correcting respective amplitude changes caused by the respective mean-blood-pressure deviations. More specifically described, in the case where a pulse pressure of one pulse of the pressure pulse wave is changed due to atrial fibrillation, a second correction factor $K_{2n}$ corrects an amplitude corresponding to the estimated mean blood pressure at that time, to an amplitude corresponding to the proper mean blood pressure $BP_{AVE}$ of the patient, i.e., a proper pressure difference $\Delta P$. For example, if an amplitude of the cuff pulse wave that corresponds to a pressure difference (=cuff pressure−estimated mean blood pressure) obtained based on the estimated mean blood pressure at the time of changing of pulse pressure is "1", and an amplitude of the cuff pulse wave that corresponds to a pressure difference $\Delta P$ (=cuff pressure−mean blood pressure $BP_{AVE}$) that would be obtained based on the mean blood pressure $BP_{AVE}$ at that time is "1.2", the second correction factor $K_{2n}$ for correcting the amplitude of the cuff pulse wave at that time is determined as being equal to "1.2".

A cuff-pulse-wave-amplitude correcting means 78 multiples each of the respective amplitudes $A_n$ of the pulses $WK_n$ of the actual cuff pulse wave, by a corresponding one of the pulse-pressure or first correction factors $K_{1n}$ determined by the pulse-pressure-correction-factor determining means 64 and a corresponding one of the mean-blood-pressure or second correction factors $K_{2n}$, and thereby provides the respective corrected amplitudes $A_n'$ of the pulses $WK_n$. That is, the amplitude correcting means 78 calculates the respective corrected amplitudes $A_n'$ of the pulses $WK_n$, according to Expression 2:

$$A_n'=A_n \times K_{1n} \times K_{2n} \quad \text{(Expression 2)}$$

A blood-pressure determining means 80 determines, based on an envelope defined by the corrected amplitudes $A_n'$ of the pulses $WK_n$ of the cuff pulse wave, corrected by the cuff-pulse-wave-amplitude correcting means 78, a proper systolic blood pressure $BP_{SYS}$, a proper diastolic blood pressure $BP_{DIA}$, a proper mean blood pressure value $BP_{MEAN}$, etc. of the patient, according to the oscillometric method, and operates the display device 36 to display the thus determined systolic blood pressure $BP_{SYS}$, diastolic blood pressure $BP_{DIA}$, etc.

Since, generally, the magnitude of the center of gravity of the area defined by the pulse-pressure waveform may be replaced with one third of the pulse pressure PM, a mean blood pressure $BP_{MEAN}$ of the patient may be obtained by adding, to the diastolic blood pressure $BP_{DIA}$, one third of the pulse pressure PM as an additional amount $\alpha$; and a middle blood pressure $BP_{MID}$ of the patient is also obtained by adding, to the diastolic blood pressure $BP_{DIA}$, half the pulse pressure PM as the additional amount $\alpha$. Therefore, when the pulse pressure PM is replaced with an estimated pulse pressure EPM determined by an estimated-pulse-pressure determining means, an estimated systolic blood pressure $EBP_{SYS}$, an estimated diastolic blood pressure $EBP_{DIA}$, an estimated mean blood pressure $EBP_{MEAN}$ and an estimated middle blood pressure $BP_{MID}$ of the patient can also be obtained.

Figure 5:
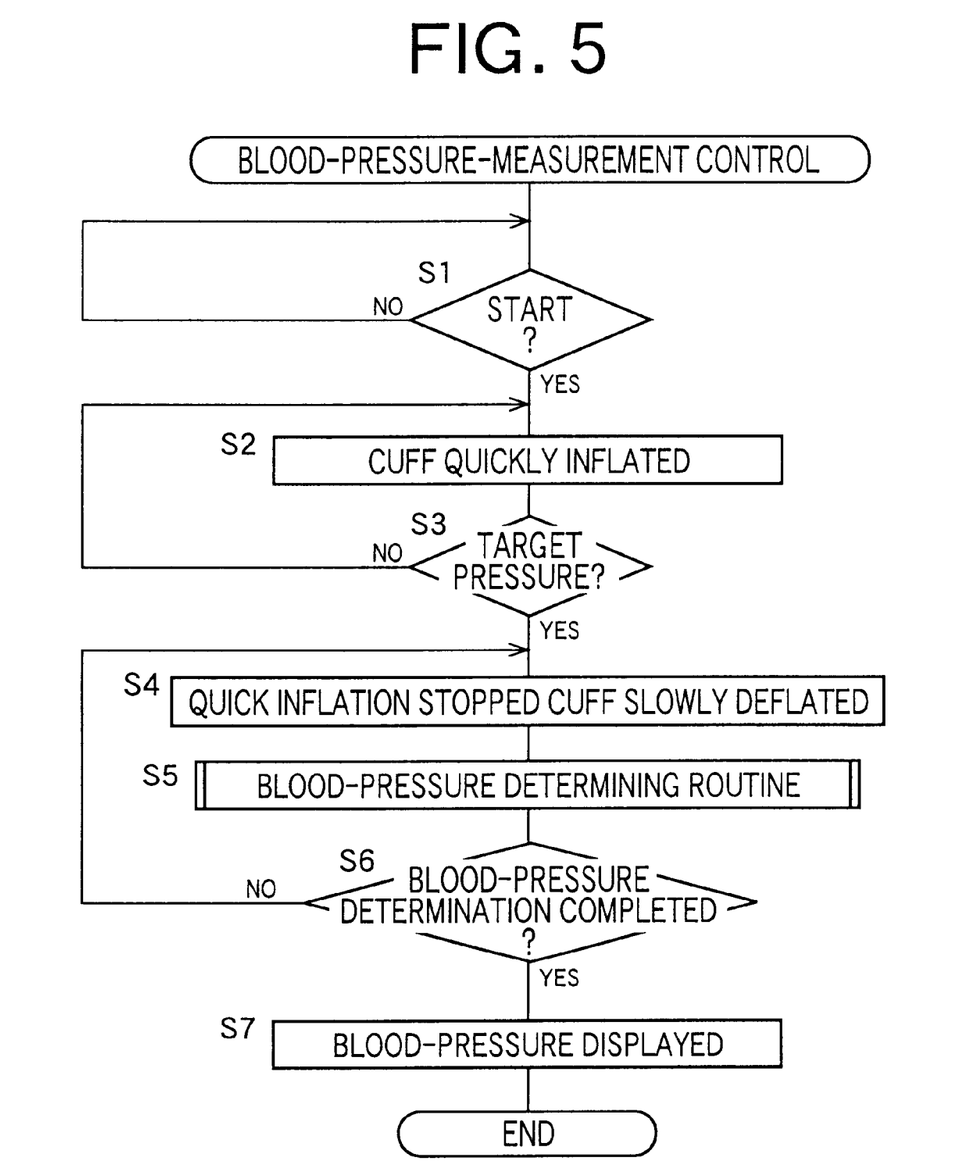
FIG. 5 is a flow chart representing a main routine according to which the essential control functions of the control device of the apparatus of FIG. 3 operate.
Figure 6:
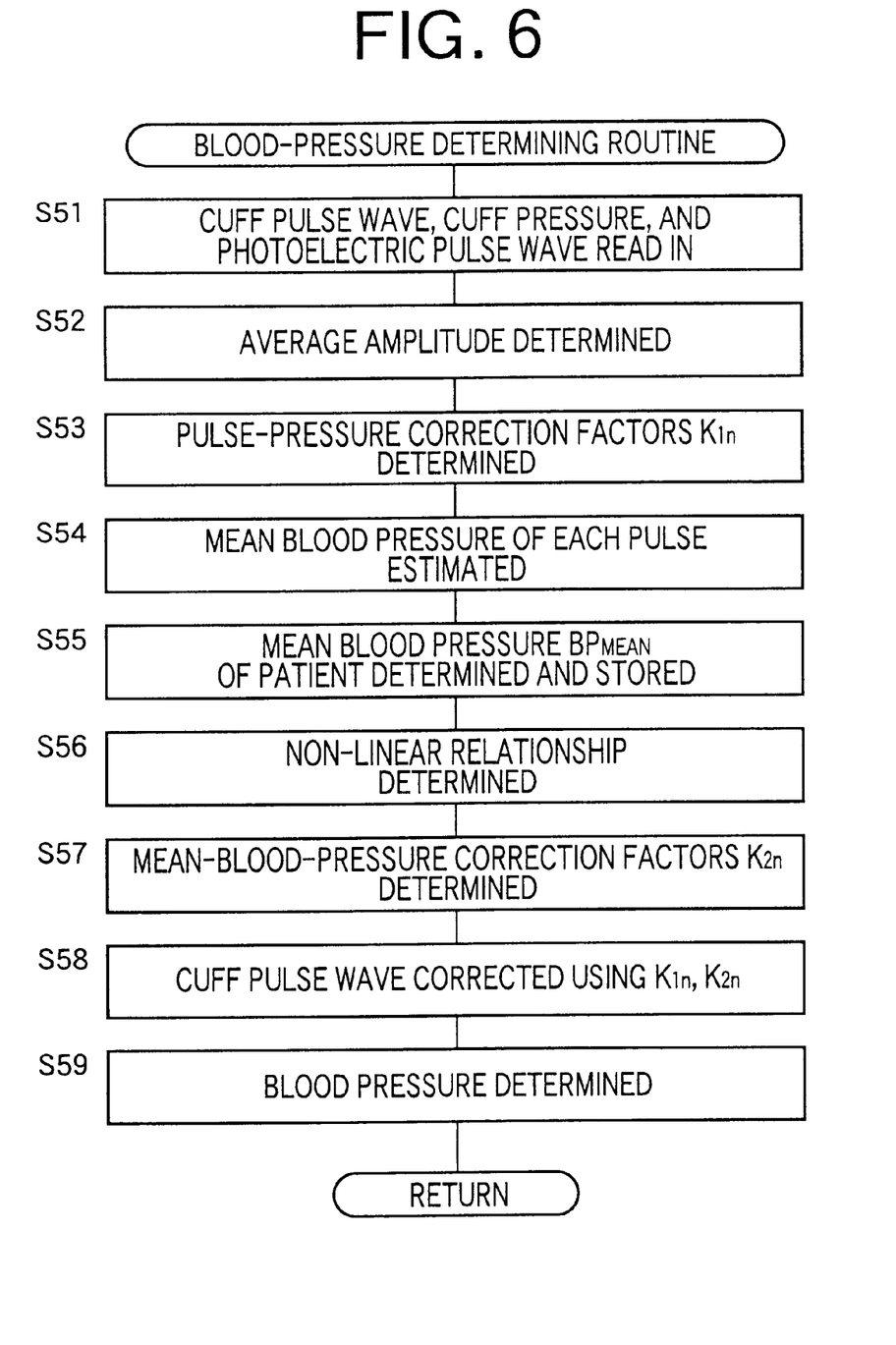
FIG. 6 is a flow chart representing a blood-pressure determining routine according to which the essential control functions of the control device of the apparatus of FIG. 3 operate.

FIGS. 5 and 6 are flow charts representing the essential control functions of the control device 28. FIG. 5 shows a blood-pressure-measurement controlling routine, and FIG. 6 shows a blood-pressure determining routine.

In FIG. 5, at Step S1 (hereinafter, "Step" is omitted), the control device judges whether a starting operation for starting the automatic blood-pressure measuring apparatus 8 has been carried out, or whether a starting condition has been satisfied. S1 is repeated till a positive judgment is made. If a positive judgment is made at S1, then the control goes to S2 to switch the deflation control valve 16 to its pressure-supply position and operates the air pump 18, so that quick inflation of the cuff 10 is started for a blood-pressure measurement. Then, at S3, the control device judges whether the cuff pressure $P_C$ has been increased up to the first target pressing pressure $P_{CM1}$, e.g., 180 mmHg. If a negative judgment is made at S3, S2 and the following step are repeated, so that the increasing of the cuff pressure $P_C$ is continued.

Meanwhile, if the cuff pressure $P_C$ is increased and a positive judgment is made at S3, the control goes to S4 to stop the air pump 18 and switch the deflation control valve 16 to its slow-deflation position, so that the cuff pressure $P_C$ is decreased at a low rate of, e.g., 3 mmHg/sec. Subsequently, at S5, the control device carries out, during the slow decreasing of the cuff pressure $P_C$, the blood-pressure determining routine, shown in FIG. 6, according to which blood pressure values are determined based on the cuff-pulse-wave signal $SM_1$ supplied from the pulse-wave filter circuit 24 and the photoelectric-pulse-wave signal $SM_2$ supplied from the photoelectric-pulse-wave sensor 40.

In FIG. 6, at S51, the control device continuously reads in, during the slow decreasing of the cuff pressure $P_C$, the cuff-pressure signal SC supplied from the static-pressure filter circuit 22, the cuff-pulse-wave signal $SM_1$ supplied from the pulse-wave filter circuit 24, and the photoelectric-pulse-wave signal $SM_2$ supplied from the photoelectric-pulse-wave sensor 40. Then, the control goes to S52 corresponding to the average-amplitude determining means 62. At S52, the control device determines respective amplitudes $AL_n$ of respective pulses $WL_n$ of the photoelectric pulse wave continuously detected by the photoelectric-pulse-wave sensor 40 during the slow decreasing of the cuff pressure $P_C$, and determines an average of the thus determined amplitudes $AL_n$, i.e., an average amplitude $AL_{per}$. Subsequently, the control goes to S53 corresponding to the pulse-pressure-correction-factor determining means 64. At S53, the control device determines a ratio of the average amplitude $AL_{per}$ to each of the respective amplitudes $AL_n$ of the pulses $WL_n$ of the photoelectric pulse wave, and thereby provides respective pulse-pressure correction factors $K_{1n}$ for the respective pulses $WL_n$ corresponding to respective pulse pressures (=systolic blood pressure−diastolic blood pressure) of respective pulses of a pressure pulse wave produced in an artery during the pressing of the cuff 10. Then, the control goes to S54 corresponding to the mean-blood-pressure estimating means 66. At S54, the control device determines, based on respective magnitudes of the respective pulses $WL_n$ corresponding to the respective pulses of the pressure pulse wave, respective estimated mean blood pressure values corresponding to the respective pulses of the pressure pulse wave.

Then, the control goes to S55 corresponding to the mean-blood-pressure determining means 70 and the mean-blood-pressure storing means 72. At S55, first, the control device determines a mean blood pressure $BP_{MEAN}$ of the patient, i.e., a temporary mean blood pressure $BP_{AVE}$ of the patient (or the subject) as a cuff pressure corresponding to the greatest amplitude of the envelope defined by the cuff pulse wave before correction, and then stores the temporary mean blood pressure $BP_{AVE}$ in a prescribed memory area. Subsequently, the control goes to S56 corresponding to the relationship determining means 74. At S56, the control device determines an S-shaped non-linear relationship between pressure difference $\Delta P$ as difference between cuff pressure and subject's mean blood pressure, and amplitude of cuff pulse wave as volumetric pulse wave, based on the mean blood pressure determined by the mean-blood-pressure determining means 70 and the actual amplitude corresponding to the mean blood pressure, e.g., as shown in FIG. 2.

Then, the control goes to S57 corresponding to the mean-blood-pressure-correction-factor determining means 76. At S57, the control device determines, according to the non-linear relationship determined at S56, respective mean-blood-pressure correction factors $K_{2n}$ for the respective pulses of the cuff pulse wave, based on respective deviations (i.e., respective differences) of the respective estimated mean blood pressure values corresponding to the respective pulses of the cuff pulse wave, estimated at S54, from the mean blood pressure $PB_{AVE}$ of the patient as the subject, stored at S55. The respective mean-blood-pressure correction factors $K_{2n}$ are for correcting respective amplitude changes caused by the respective mean-blood-pressure deviations. Subsequently, the control goes to S58 corresponding to the cuff-pulse-wave-amplitude correcting means 78. At S58, the control device multiples each of respective amplitudes An of respective pulses $WK_n$ of the actual cuff pulse wave by a corresponding one of the pulse-pressure correction factors $K_{1n}$ and a corresponding one of the mean-blood-pressure correction factors $K_{2n}$, and thereby provides the respective corrected amplitudes $A_n'$ of the pulses $WK_n$.

Then, the control goes to S59 corresponding to the blood-pressure determining means 80. At S59, the control device determines, based on an envelope defined by the corrected amplitudes $A_n'$ of the pulses $WK_n$ of the cuff pulse wave, a systolic blood pressure $BP_{SYS}$, a diastolic blood pressure $BP_{DIA}$, etc. of the patient, according to the oscillometric method.

Then, the control goes to S6 of FIG. 5 to judge whether the determination of blood pressure values have been completed. Initially, a negative judgment is made at S6, and accordingly S4 and the following steps are repeated. Meanwhile, if a positive judgment is made at S6, the control goes to S7 to operate the display device 36 to display the thus determined systolic blood pressure $BP_{SYS}$, diastolic blood pressure $BP_{DIA}$, etc.

It emerges from the foregoing description that in the present embodiment, the cuff-pulse-wave-amplitude correcting means 78 (S57) corrects the respective amplitudes of the respective pulses of the cuff pulse wave, according to the non-linear relationship between pressure difference $\Delta P$ as difference between cuff pressure and subject's mean blood pressure, and amplitude of cuff pulse wave, and the blood-pressure determining means 80 (S59) determines the systolic blood pressure $BP_{SYS}$, diastolic blood pressure $BP_{DIA}$, etc. of the subject based on the change of the corrected amplitudes of the cuff pulse wave. Thus, even in the case where arrhythmia occurs, a reliable envelope is obtained and accordingly a blood pressure can be measured or an accurate blood pressure can be obtained.

In addition, the present embodiment relates to the oscillometric automatic blood-pressure measuring apparatus 8, including the cuff 10 which is wound around a prescribed portion of a living subject, and determining a blood pressure of the subject based on change of amplitudes of respective pulses of a cuff pulse wave as an oscillatory component produced in synchronism with pulsation in the cuff during a slow cuff-pressure change process in which a cuff pressure as a pressure in the cuff is slowly changed, the apparatus further including (a) the pulse-wave filter circuit 24 (the pulse-wave detecting device) which is associated with a prescribed portion of the subject and which continuously detects a pulse wave from the prescribed portion, (b) the pulse-pressure-correction-factor determining means 64 (S53) for determining, based on respective amplitudes of respective pulses of the pulse wave detected by the pulse-wave detecting device, respective pulse-pressure correction factors $K_{1n}$ to correct respective pulse pressures corresponding to the respective amplitudes of the pulse wave, to a single value, (c) the mean-blood-pressure determining means 70 (S55) for determining a mean blood pressure of the subject based on the cuff pulse wave, (d) the relationship determining means 74 (S56) for determining, based on the mean blood pressure determined by the mean-blood-pressure determining means 70, the non-linear relationship between pressure difference as difference between cuff pressure and subject's mean blood pressure, and amplitude of cuff pulse wave, (e) the mean-blood-pressure estimating means 66 (S54) for estimating, based on the pulse wave detected by the pulse-wave detecting device, respective estimated mean blood pressure values corresponding to respective pulses of the cuff pulse wave, (f) the mean-blood-pressure-correction-factor determining means 76 (S57) for determining, according to the relationship determined by the relationship determining means 74, respective mean-blood-pressure correction factors $K_{2n}$ to correct respective amplitude changes caused by respective deviations of the respective estimated mean blood pressure values corresponding to the respective pulses of the cuff pulse wave, from the mean blood pressure, (g) the cuff-pulse-wave-amplitude correcting means 78 (S58) for correcting the respective amplitudes of the respective pulses of the cuff pulse wave, based on the respective pulse-pressure correction factors $K_{1n}$ determined by the pulse-pressure-correction-factor determining means 64 and the respective mean-blood-pressure correction factors $K_{2n}$ determined by the mean-blood-pressure-correction-factor determining means 76, and (h) the blood-pressure determining means 80 for determining the blood pressure of the subject based on the change of the corrected amplitudes of the cuff pulse wave. The envelope defined by the corrected cuff pulse wave is accurate, and the blood pressure can be easily determined based on the envelope. Thus, even in the case where arrhythmia occurs, a blood pressure can be measured or an accurate blood pressure can be obtained.

In addition, the present apparatus further includes the temporary-mean-blood-pressure determining means 70 for determining, as the temporary mean blood pressure of the subject, the cuff pressure corresponding to the greatest one of the amplitudes of the cuff pulse wave by using an envelope defined by the amplitudes before correction, and the mean-blood-pressure storing means 72 stores the temporary mean blood pressure determined by the mean-blood-pressure determining means 70. Thus, an accurate mean blood pressure of the subject is obtained as compared with the case where a mean blood pressure measured in the last measurement is used, and accordingly a blood pressure can be measured with higher accuracy even in the case where arrhythmia occurs.

While the present invention has been described in detail in one embodiment thereby by reference to the drawings, the present invention may otherwise be embodied.

For example, in the illustrated embodiment, the blood-pressure determining routine is carried out during the slow decreasing of the pressure in the cuff 10. However, it is possible to carry out the blood-pressure determining routine during a slow increasing of the pressure in the cuff 10.

In addition, in the illustrated embodiment, the transmission-type photoelectric-pulse-wave sensor 40 that detects the change of volume of blood based on the amount of transmitted light, is employed as the volumetric-pulse-wave detecting device. However, it is possible to employ, as the volumetric-pulse-wave detecting device, a reflection-type photoelectric-pulse-wave sensor that detects the change of volume of blood based on the amount of reflected light; an impedance-pulse-wave detecting device which detects the change of volume of blood based on the change of impedance between prescribed regions of a living subject; or a volume-change detecting device that wraps, e.g., a tip of a finger and detects the change of volume of blood based on the change of volume of that region. In addition, the volumetric-pulse-wave detecting device may be replaced with a pressure-pulse-wave detecting device that presses an artery and thereby detects a pressure pulse wave.

Moreover, in the illustrated embodiment, the cuff-pulse-wave-amplitude correcting means 78 corrects the amplitudes of the cuff pulse wave based on both the pulse-pressure correction factors $K_{1n}$ and the mean-blood-pressure correction factors $K_{2n}$. However, the correcting means 78 may be arranged to correct the amplitudes of the cuff pulse wave, based on only the mean-blood-pressure correction factors $K_{2n}$, to some advantage.

The present invention may be embodied with various changes without departing from the spirit thereof.

What is claimed is:

1. An oscillometric automatic blood-pressure measuring apparatus, comprising:

an inflatable cuff which is adapted to be wound around a first portion of a living subject, so as to detect respective amplitudes of a plurality of heartbeat-synchronous pulses of a cuff pulse wave as an oscillatory component that is produced in the cuff in synchronism with heartbeats of the subject in a cuff-pressure change process in which a cuff pressure as a pressure in the cuff is changed;

a cuff-pulse-wave-amplitude correcting means for correcting the respective amplitudes of the respective pulses of the cuff pulse wave, according to a predetermined non-linear relationship between difference between cuff pressure and subject's mean blood pressure, and amplitude of cuff pulse wave: and a blood-pressure determining means for determining a blood pressure of the subject based on a change of the corrected amplitudes of the cuff pulse wave.

2. An apparatus according to claim 1, wherein the blood-pressure determining means determines at least one of a systolic blood pressure and a diastolic blood pressure of the subject based on at least one change of the corrected amplitudes of the cuff pulse wave.

3. An apparatus according to claim 1, further comprising a cuff-pressure sensor which detects the cuff pressure as the pressure in the cuff.

4. An apparatus according to claim 1, further comprising a cuff-pulse-wave detecting device which detects, from the cuff, the respective heartbeat-synchronous pulses of the cuff pulse wave as a first volumetric pulse wave.

5. An apparatus according to claim 4, further comprising:

a second-volumetric-pulse-wave detecting device which is worn on a second portion of the subject and which detects, from the second portion, a plurality of heartbeat-synchronous pulses of a second volumetric pulse wave; and a first-correction-factor determining means for determining, based on respective amplitudes of the respective pulses of the second volumetric pulse wave, respective first correction factors which can modify the respective amplitudes of the respective pulses of the second volumetric pulse wave, to a single value, and accordingly correct the respective amplitudes of the respective pulses of the cuff pulse wave as the first volumetric pulse wave.

6. An apparatus according to claim 5, further comprising a mean-blood-pressure determining means for determining a mean blood pressure of the subject based on the respective amplitude of the respective pulses of the cuff pulse wave that have not been corrected by the cuff-pulse-wave-amplitude correcting means, wherein the mean-blood-pressure storing device stores the mean blood pressure determined by the mean-blood-pressure determining means.

7. An apparatus according to claim 6, further comprising:

a mean-blood-pressure estimating means for estimating, based on the respective pulses of the second volumetric pulse wave detected by the second-volumetric-pulse-wave detecting device, respective estimated mean blood pressure values corresponding to the respective pulses of the cuff pulse wave as the first volumetric pulse wave; and a second-correction-factor determining means for determining, according to the non-linear relationship determined by the relationship determining means, respective second correction factors which correct respective amplitude changes caused by respective deviations of the respective estimated mean blood pressure values corresponding to the respective pulses of the cuff pulse wave, from the mean blood pressure stored by the mean-blood-pressure storing device, wherein the cuff-pulse-wave-amplitude correcting means corrects the respective amplitudes of the respective pulses of the cuff pulse wave, based on the first correction factors determined by the first-correction-factor determining means and the second correction factors determined by the second-correction-factor determining means.

8. An apparatus according to claim 1, further comprising a display device which displays the blood pressure of the subject determined by the blood-pressure determining means.

9. An oscillometric automatic blood-pressure measuring apparatus, comprising:

an inflatable cuff which is adapted to be wound around a first portion of a living subject, so as to detect respective amplitudes of a plurality of heartbeat-synchronous pulses of a cuff pulse wave as an oscillatory component that is produced in the cuff in synchronism with heartbeats of the subject in a cuff-pressure change process in which a cuff pressure as a pressure in the cuff is changed;

a pulse-wave detecting device which is worn on a second portion of the subject and which detects, from the second portion, a plurality of heartbeat-synchronous pulses of a pulse wave;

a pulse-pressure-correction-factor determining means for determining, based on respective amplitudes of the respective pulses of the pulse wave detected by the pulse-wave detecting device, respective pulse-pressure correction factors to correct respective pulse pressures corresponding to the respective amplitudes of the respective pulses of the pulse wave, to a single value;

a mean-blood-pressure storing device which stores a mean blood pressure of the subject;

a relationship determining means for determining, based on the mean blood pressure stored by the mean-blood-pressure storing device, a non-linear relationship between difference between cuff pressure and subject's mean blood pressure, and amplitude of cuff pulse wave;

a mean-blood-pressure estimating means for estimating, based on the respective pulses of the pulse wave detected by the pulse-wave detecting device, respective estimated mean blood pressure values corresponding to the respective pulses of the cuff pulse wave;

a mean-blood-pressure-correction-factor determining means for determining, according to the non-linear relationship determined by the relationship determining means, respective mean-blood-pressure correction factors to correct respective amplitude changes corresponding to respective deviations of the respective estimated mean blood pressure values corresponding to the respective pulses of the cuff pulse wave, from the mean blood pressure stored by the mean-blood-pressure storing device;

a cuff-pulse-wave-amplitude correcting means for correcting the respective amplitudes of the cuff pulse wave, based on the respective pulse-pressure correction factors determined by the pulse-pressure-correction-factor determining means and the respective mean-blood-pressure correction factors determined by the mean-blood-pressure-correction-factor determining means; and a blood-pressure determining means for determining a blood pressure of the subject based on a change of the corrected amplitudes of the cuff pulse wave.

10. An oscillometric automatic blood-pressure measuring apparatus according to claim 9, further comprising a temporary-mean-blood-pressure determining means for determining, as a temporary mean blood pressure of the subject, a cuff pressure corresponding to the greatest one of the respective amplitudes of the respective pulses of the cuff pulse wave by using an envelope defined by the amplitudes before correction, wherein the mean-blood-pressure storing device stores, as the mean blood pressure of the subject, the temporary mean blood pressure determined by the temporary-mean-blood-pressure determining means.

* * * * *